US 11,529,525 B2

(12) United States Patent
English et al.

(10) Patent No.: US 11,529,525 B2
(45) Date of Patent: Dec. 20, 2022

(54) LEAD RETENTION METHOD

(71) Applicant: Cardiac Pacemakers, Inc., St. Paul, MN (US)

(72) Inventors: James M. English, Cahir (IE); Moira B. Sweeney, St. Paul, MN (US); John O'Rourke, Clonmel (IE); Robert A. Jones, Lake Elmo, MN (US); Trey H. Achterhoff, St. Paul, MN (US); Scott A. Spadgenske, Buffalo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 17/032,057

(22) Filed: Sep. 25, 2020

(65) Prior Publication Data

US 2021/0085984 A1  Mar. 25, 2021

Related U.S. Application Data

(60) Provisional application No. 62/905,666, filed on Sep. 25, 2019.

(51) Int. Cl.
*A61N 1/375* (2006.01)
*A61N 1/39* (2006.01)

(52) U.S. Cl.
CPC ........ *A61N 1/3752* (2013.01); *A61N 1/37512* (2017.08); *A61N 1/3956* (2013.01)

(58) Field of Classification Search
CPC . A61N 1/3752; A61N 1/3956; A61N 1/37512
USPC ....................................................... 607/116
See application file for complete search history.

(56) References Cited

U.S. PATENT DOCUMENTS

| 4,112,953 A * | 9/1978 | Shanker ............... A61N 1/3752 439/843 |
|---|---|---|
| 4,860,750 A | 8/1989 | Frey et al. |
| 5,413,595 A | 5/1995 | Stutz |
| 5,707,399 A | 1/1998 | Killander et al. |
| 3,108,045 A1 | 1/2012 | Biggs, Jr. et al. |
| 2010/0197174 A1 | 8/2010 | Lahti et al. |
| 2016/0375255 A1 | 12/2016 | Janzig et al. |
| 2018/0200511 A1 | 7/2018 | Ramesh et al. |

FOREIGN PATENT DOCUMENTS

EP          0930913 A          7/1999

OTHER PUBLICATIONS

International Search Report and Written Opinion issued in PCT/US2020/052614, dated Dec. 16, 2020, 14 pages.
International Preliminary Report on Patentability, dated Mar. 15, 2022, 7 pages.

* cited by examiner

*Primary Examiner* — Nadia A Mahmood
(74) *Attorney, Agent, or Firm* — Nelson Mullins Riley & Scarborough LLP (57) ABSTRACT

Various aspects of the present disclosure are directed toward apparatuses, systems and methods for connecting a lead to an implantable medical device. The apparatuses, systems and methods may include a clamp arranged within a connector port configured to secure the lead with a header in response to frictional engagement between a portion of the implantable lead and the clamp.

19 Claims, 8 Drawing Sheets

LEAD RETENTION METHOD

CROSS REFERENCE TO RELATED APPLICATION

This application claims priority to Provisional Application No. 62/950,666, filed Sep. 25, 2019, which is herein incorporated by reference in its entirety.

TECHNICAL FIELD

The present disclosure relates to an implantable system having an implantable lead and a connector port. More specifically, the disclosure relates to releasably securing of the implantable lead within the connector port.

BACKGROUND

Implantable medical systems may include an implantable lead assembly and an implantable pulse generator connected with the implantable lead assembly. Further, a header of the implantable pulse generator generally includes corresponding connector ports to effectively couple the lead assembly with the implantable pulse generator. A proper connection between the implantable leads and the corresponding connector ports is required to allow proper functioning of the implantable system. The lead assembly and the implantable pulse generator are to remain connected after implantation to ensure desired functionality.

SUMMARY

In Example 1, an implantable medical device includes a housing; and a header arranged with the housing; a connector port arranged within the header and configured to couple an implantable lead to the header; and a clamp arranged within the connector port configured to secure the implantable lead with the header in response to frictional engagement between a portion of the implantable lead and the clamp.

In Example 2, the implantable medical device of Example 1, wherein the clamp includes an engagement portion configured to receive the portion of the implantable lead and the clamp and a securement portion configured to reduce a diameter of the engagement portion to frictionally engage the portion of the implantable lead.

In Example 3, the implantable medical device of Example, wherein the securement portion includes at least one wedge portion configured to reduce the diameter of the engagement portion to frictionally engage the portion of the implantable lead.

In Example 4, the implantable medical device of any one of Examples 1-3, wherein the connector port includes a proximal end and a distal end with the clamp being arranged between the proximal end and the distal end of the connector port, and the clamp is configured to maintain the portion of the implantable lead within the connector port in response to forces acting on the implantable lead in a direction opposite the distal end.

In Example 5, the implantable medical device of Example 4, wherein the clamp is configured to increase frictional hold on the portion of the implantable lead in response to the forces acting on the implantable lead in the direction opposite the distal end.

In Example 6, the implantable medical device of Example 5, wherein the clamp is configured to progressively increase the frictional hold on the portion of the implantable lead in response to the increasing forces acting on the implantable lead in the direction opposite the distal end.

In Example 7, the implantable medical device of any one of Examples 1-6, wherein the clamp is configured to maintain securement between the portion of the implantable lead and the connector port in the absence of disengagement of the clamp.

In Example 8, the implantable medical device of Example 7, further comprising a release mechanism arranged on the header and configured to disengage the clamp in response to a force applied to the release mechanism.

In Example 9, the implantable medical device of Example 8, wherein the release mechanism includes a button configured to disengage the clamp in response to the force applied by a user.

In Example 10, the implantable medical device of any one of Examples 8-9, wherein the release mechanism includes at least one release portion configured to interact with the clamp to block frictional engagement between the portion of the implantable lead and the clamp.

In Example 11, the implantable medical device of Example 8, wherein the clamp is configured to allow engagement between the portion of the implantable lead and the clamp while the force is applied to the release mechanism, and lock the portion of the implantable lead within the clamp in response to the release of the force on the release mechanism.

In Example 12, the implantable medical device of any one of Examples 1-10, further comprising a spring arranged within the connector port and configured to bias the clamp to facilitate frictional engagement between the portion of the implantable lead and the clamp.

In Example 13, the implantable medical device of Example 12, wherein the clamp is configured to lock the portion of the implantable lead within the clamp in response to the frictional engagement between the portion of the implantable lead and the clamp.

In Example 14, the implantable medical device of any one of Examples 1-10, wherein the clamp is configured to lock the portion of the implantable lead within the clamp in response to a first force applied to the implantable lead in a first direction to engage the clamp and a second force applied to the implantable lead in a second direction opposite the first direction.

In Example 15, the implantable medical device of any one of Examples 1-14, further includes surface structures arranged within the clamp to facilitate frictional engagement between the portion of the implantable lead and the clamp.

In Example 16, an implantable medical device includes a housing; and a header arranged with the housing; a connector port arranged within the header and configured to couple an implantable lead to the header; and a clamp arranged within the connector port configured to secure the implantable lead with the header, the clamp including an engagement portion configured to receive a portion of the implantable lead and a securement portion configured to reduce a diameter of the engagement portion to frictionally engage the portion of the implantable lead.

In Example 17, the implantable medical device of Example 16, wherein the securement portion is configured to apply force inwardly relative to the connector port in response to the engagement between the portion of the implantable lead and the engagement portion.

In Example 18, the implantable medical device of Example 17, wherein the securement portion includes angled surfaces extending from the engagement portion, and the angled surfaces are configured to apply force against opposing angled faces on the connector port to reduce the diameter of the engagement portion to frictionally engage the portion of the implantable lead.

In Example 19, the implantable medical device of Example 18, wherein the angled surfaces of the securement portion are configured to apply force inwardly relative to the connector port to reduce the diameter of the engagement portion.

In Example 20, the implantable medical device of Example 18, wherein the angled surfaces of the securement portion each include a protrusion extending outwardly relative to the angled surfaces of the securement portion configured to apply force against the opposing angled faces on the connector port to reduce the diameter of the engagement portion.

In Example 21, the implantable medical device of Example 16, further comprising a release mechanism arranged on the header and configured to disengage the clamp in response to a force applied to the release mechanism to release the portion of the implantable lead from the clamp.

In Example 22, the implantable medical device of Example 21, wherein the release mechanism includes a button configured to disengage the clamp in response to the force applied by a user.

In Example 23, the implantable medical device of Example 21, wherein the release mechanism includes at least one release portion configured to interact with the securement portion to enable disengagement of the portion of the implantable lead from the engagement portion.

In Example 24, the implantable medical device of Example 23, wherein the at least one release portion is configured to block movement of the securement portion to expand the engagement portion and enable disengagement of the portion of the implantable lead from the engagement portion.

In Example 25, the implantable medical device of Example 21, wherein the clamp is configured to allow engagement between the portion of the implantable lead and the engagement portion while the force is applied to the release mechanism, and lock the portion of the implantable lead within the engagement portion in response to the release of the force on the release mechanism.

In Example 26, the implantable medical device of Example 16, further including a spring arranged within the connector port and configured to bias the securement portion to reduce the diameter of the engagement portion to facilitate frictional engagement between the portion of the implantable lead and the engagement portion.

In Example 27, the implantable medical device of Example 26, wherein the securement portion is configured to lock the portion of the implantable lead within the engagement portion in response to the engagement between the portion of the implantable lead and the securement portion.

In Example 28, the implantable medical device of Example, wherein the securement portion is configured to lock the portion of the implantable lead within the engagement portion in response a first force applied to the implantable lead in a first direction to engage the engagement portion and a second force applied to the implantable lead in a second direction opposite the first direction.

In Example 29, an implantable medical device includes a housing; and a header arranged with the housing; a connector port arranged within the header and configured to couple an implantable lead to the header; a clamp arranged within the connector port configured to releasably secure the implantable lead with the header in response to frictional engagement between a portion of the implantable lead and the clamp in response a first force applied to the implantable lead in a first direction; and a release mechanism configured to allow release of the frictional engagement between the clamp and the portion of the implantable lead and allow removal of the implantable lead from the clamp in response to a second force applied to the implantable lead in a second direction opposite the first direction.

In Example 30, the implantable medical device of Example 29, wherein the release mechanism is configured to disengage the clamp in response to a force applied to the release mechanism to release the portion of the implantable lead from the clamp.

In Example 31, the implantable medical device of Example 30, wherein the release mechanism includes a button configured to disengage the clamp in response to the force applied by a user.

In Example 32, the implantable medical device of Example 31, wherein the release mechanism includes at least one release portion configured interact with the securement portion to enable disengagement of the portion of the implantable lead from the clamp in response to the user pressing the button.

In Example 33, a method of coupling an implantable lead to an implantable medical device includes coupling the implantable lead to the implantable medical device by moving the implantable lead in a first direction into a connector port arranged within a header of the implantable medical device; and engaging a portion of the implantable lead with a clamp arranged within the connector port in response to frictional engagement between the portion of the implantable lead and the clamp.

In Example 34, the method of Example 33, further includes releasing the portion of the implantable lead by applying a force to a release mechanism arranged with the header.

In Example 35, the method of Example 34, wherein applying the force to the release mechanism includes pressing a button to block the frictional engagement between the clamp and the portion of the implantable lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
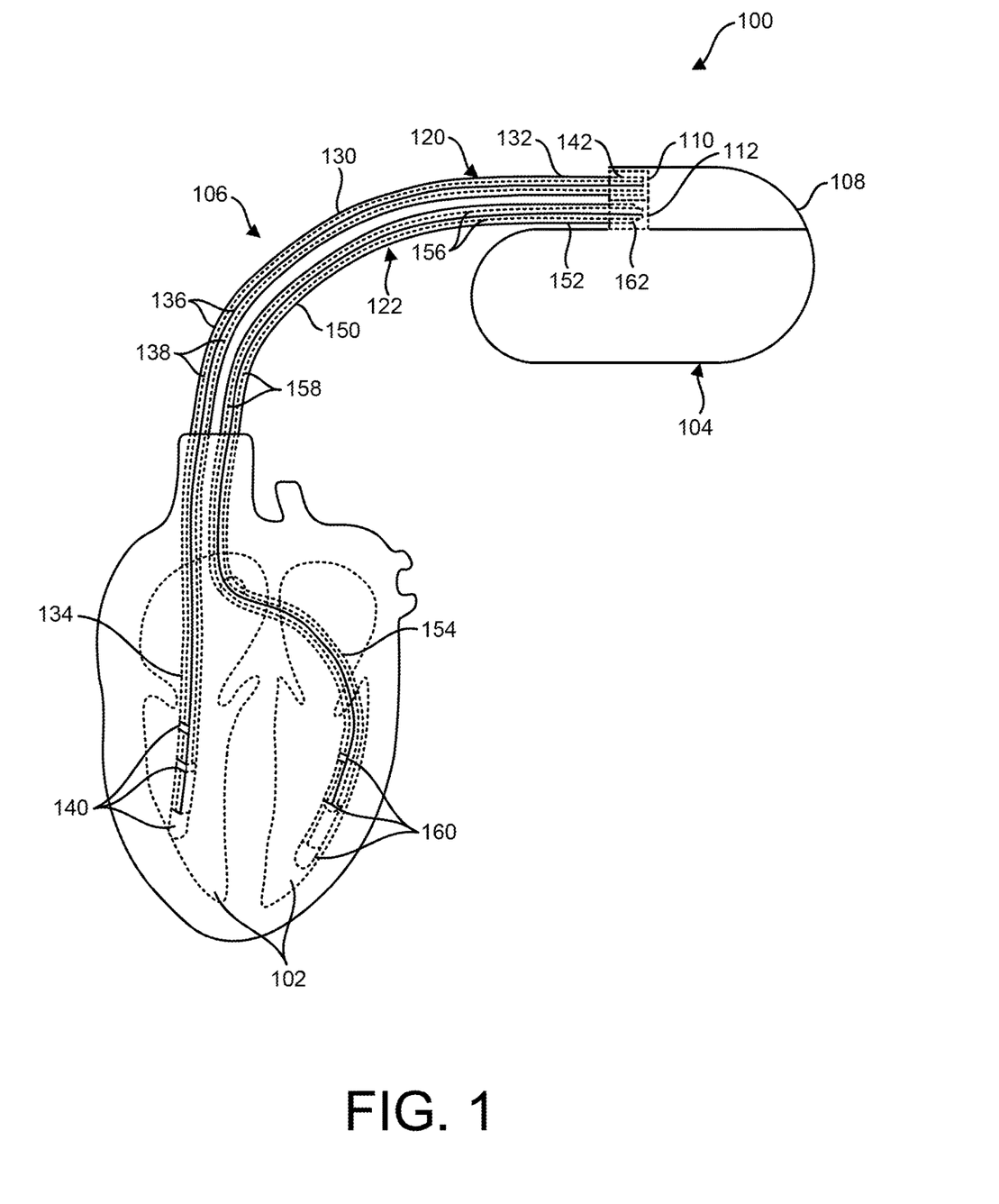
FIG. 1 is an illustration of an example implantable system for stimulating a target location on or within the heart, in accordance with various aspects of the present disclosure.

FIG. 1 is a schematic illustration of an implantable system 100 for stimulating a target location 102 on or within the heart. As shown, the implantable system 100 includes an implantable medical device (IMD) 104 and an implantable lead assembly 106 connected to the IMD 104. In various embodiments, the IMD 104 is an implantable pulse generator adapted to generate electrical signals to be delivered to the target location 102 for pacing and/or for sensing electrical activity at a location on or within the heart. The IMD 104 can include microprocessors to provide processing, evaluation, and to deliver electrical shocks and pulses of different energy levels and timing for defibrillation, cardioversion, and pacing to a heart in response to cardiac arrhythmia including fibrillation, tachycardia, heart failure, and bradycardia. In other instances, the implantable system 100 can also be suitable for use with implantable electrical stimulators, such as, but not limited to, neuro-stimulators, skeletal stimulators, central nervous system stimulators, or stimulators for the treatment of pain.

The IMD 104 may include one or more connector ports 110, 112. In certain instances, the IMD (e.g., pulse generator 104) includes a header 108 with the connector port(s) 110, 112. As shown, for example, the header 108 includes a first connector port 110 and a second connector port 112. In addition, the implantable lead assembly 106 includes a first implantable lead 120 connected to the first connector port 110 and a second implantable lead 122 connected to the second connector port 112. In some instances, the implantable lead assembly 106 may also include a third implantable lead (not shown) and the header 108 may include a corresponding third connector port (not shown).

Figure 5:
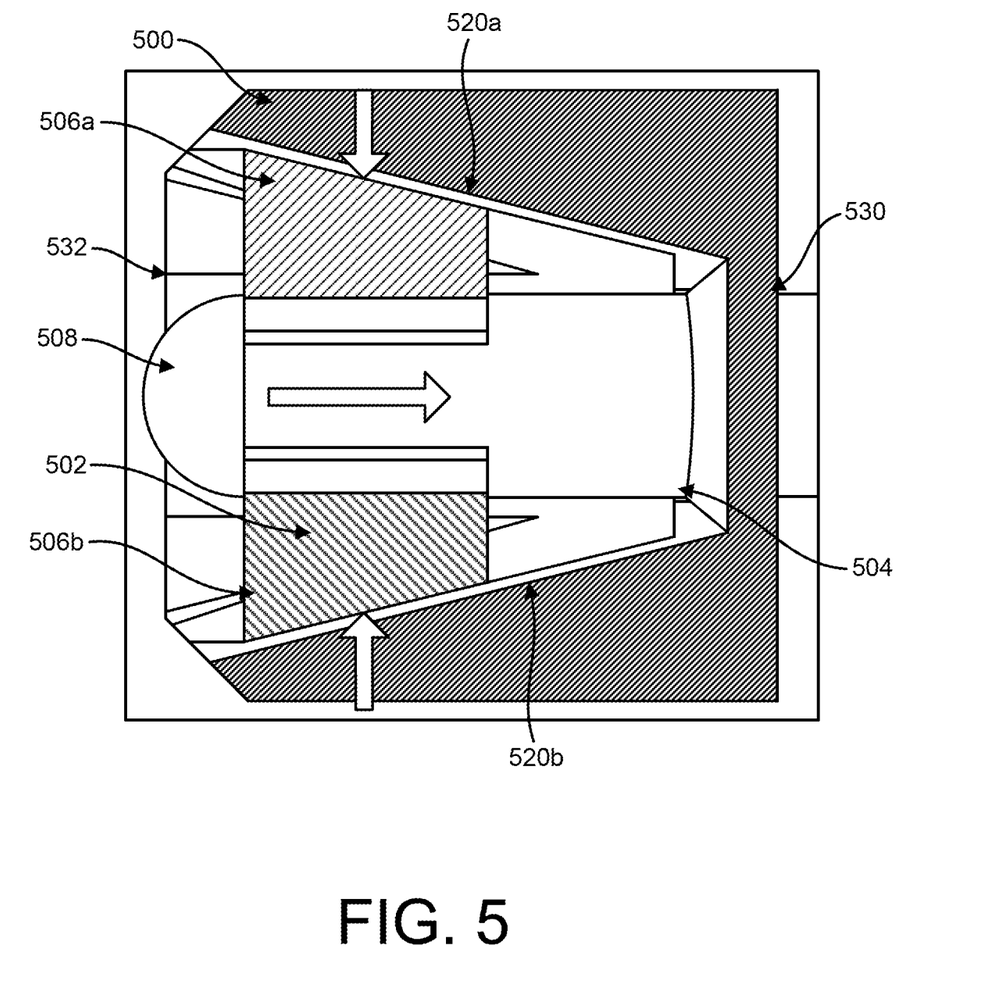
FIG. 5 is a cross-sectional view of an illustration of an example connector port and clamp, in accordance with various aspects of the present disclosure.
Figure 6:
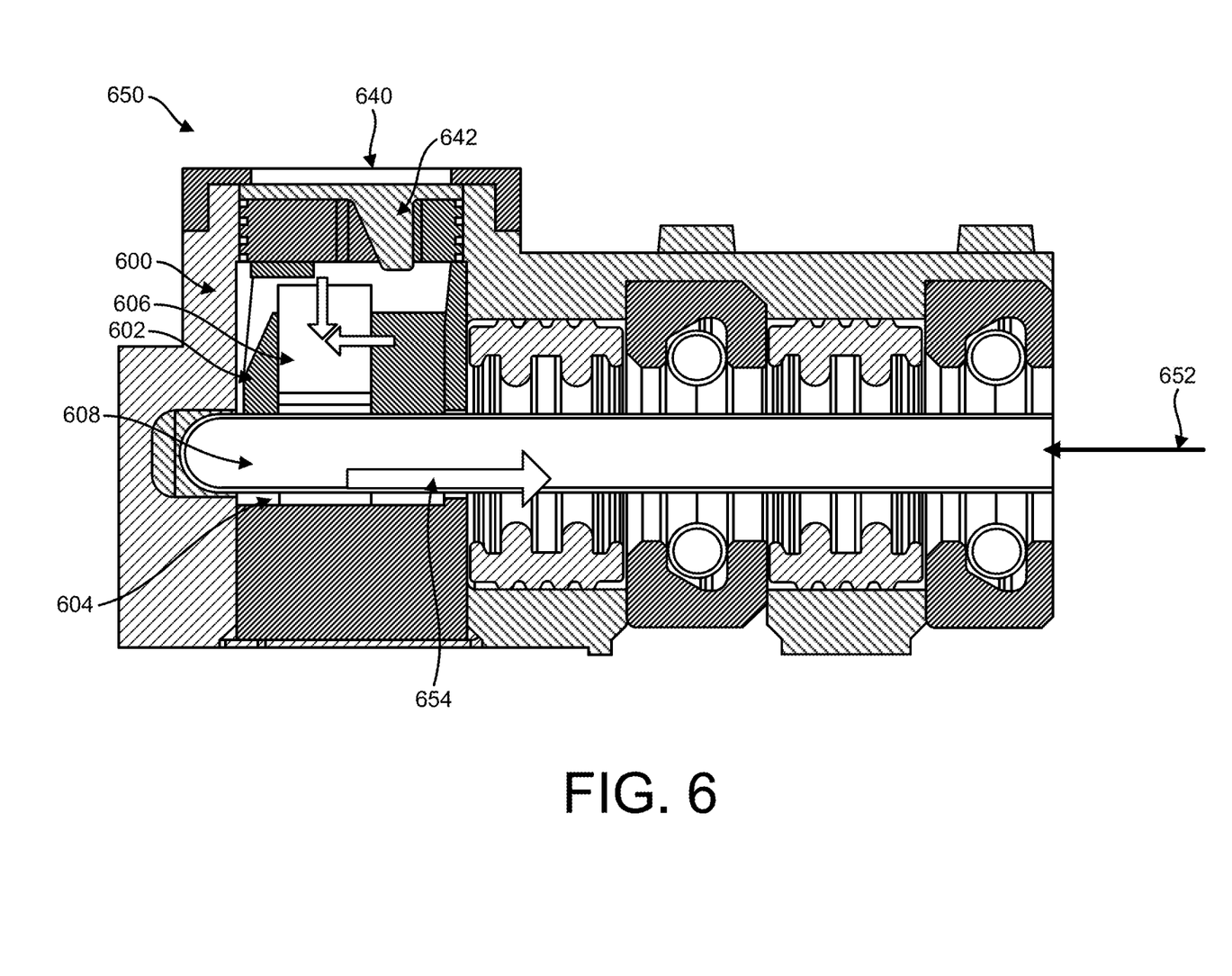
FIG. 6 is a side cross-sectional view of an illustration of an example header, connector port, and clamp, in accordance with various aspects of the present disclosure.

Each of the first and second implantable leads 120, 122 includes a flexible lead body, a plurality of conductor wires, a plurality of electrodes, and a terminal connector assembly (as shown in detail, for example, with reference to FIGS. 5-6). For example, as shown, the first implantable lead 120 includes a flexible lead body 130 having a proximal end 132, a distal end portion 134, and a plurality of conductor lumens 136 extending axially within the lead body 130 from the proximal end 132 to the distal end portion 134. The first implantable lead 120 also includes a plurality of conductor wires 138, each conductor wire extending within one of the conductor lumens 136 in the lead body 130. The first implantable lead 120 further includes a plurality of electrodes 140 coupled to the distal end portion 134 of the lead body 130. Each of the electrodes 140 is electrically coupled to at least one of the plurality of conductor wires 138. The first implantable lead 120 also includes a terminal connector assembly 142 (or terminal pin) coupled to the proximal end 132 of the lead body 130. The terminal connector assembly 142 is sized to be inserted into and received by the first connector port 110 of the header 108.

Similarly, the second implantable lead 122 includes a flexible lead body 150 having a proximal end 152, a distal end portion 154, and a plurality of conductor lumens 156 extending axially within the lead body 150 from the proximal end 152 to the distal end portion 154. The second implantable lead 122 also includes a plurality of conductor wires 158, each conductor wire extending within one of the conductor lumens 156 in the lead body 150. Further, the second implantable lead 122 includes a plurality of electrodes 160 coupled to the distal end portion 154 of the lead body 150. Each of the electrodes 160 is electrically coupled to at least one of the plurality of conductor wires 158. The second implantable lead 122 also includes a terminal connector assembly 162 coupled to the proximal end 152 of the lead body 150. The terminal connector assembly 162 is sized to be inserted into and received by the second connector port 112 of the header 108.

As an example of implant locations for one or more leads, the first implantable lead 120 is shown extending into a right ventricle of the heart, and the second implantable lead 122 extending through the coronary sinus and into a coronary vein disposed outside the left ventricle of the heart. The electrical signals and stimuli conveyed by the IMD 104 are carried to the electrode at the distal end of the lead by the conductors. The IMD 104 is typically implanted subcutaneously within an implantation location or pocket in the patient's chest or abdomen.

The IMD 104 and lead(s) 120, 122 are connected by a physician. In order to maintain the implantable leads 120, 122 connected to the IMD 104, the header 108 may include a mechanism that secures the lead(s) 120, 122 in place. In addition, the securement mechanism may be releasable, in certain instances, to allow for manipulation or replacement of the lead(s) 120, 122. As described in detail below, the securement mechanism (e.g., a clamp) may indicate to the physician that the lead(s) 120, 122 are properly secured. In addition, the securement mechanism may be passive such to facilitate ease of connection. Further, the securement mechanism lessens the ability for the lead(s) 120, 122 to be removed or back out of the header 108, without intentional intervention by the physician, after the lead(s) 120, 122 have been connected. Further yet, the securement mechanism does not require any additional tool or tooling for connection of the lead(s) 120, 122 to the header 108.

Figure 2:
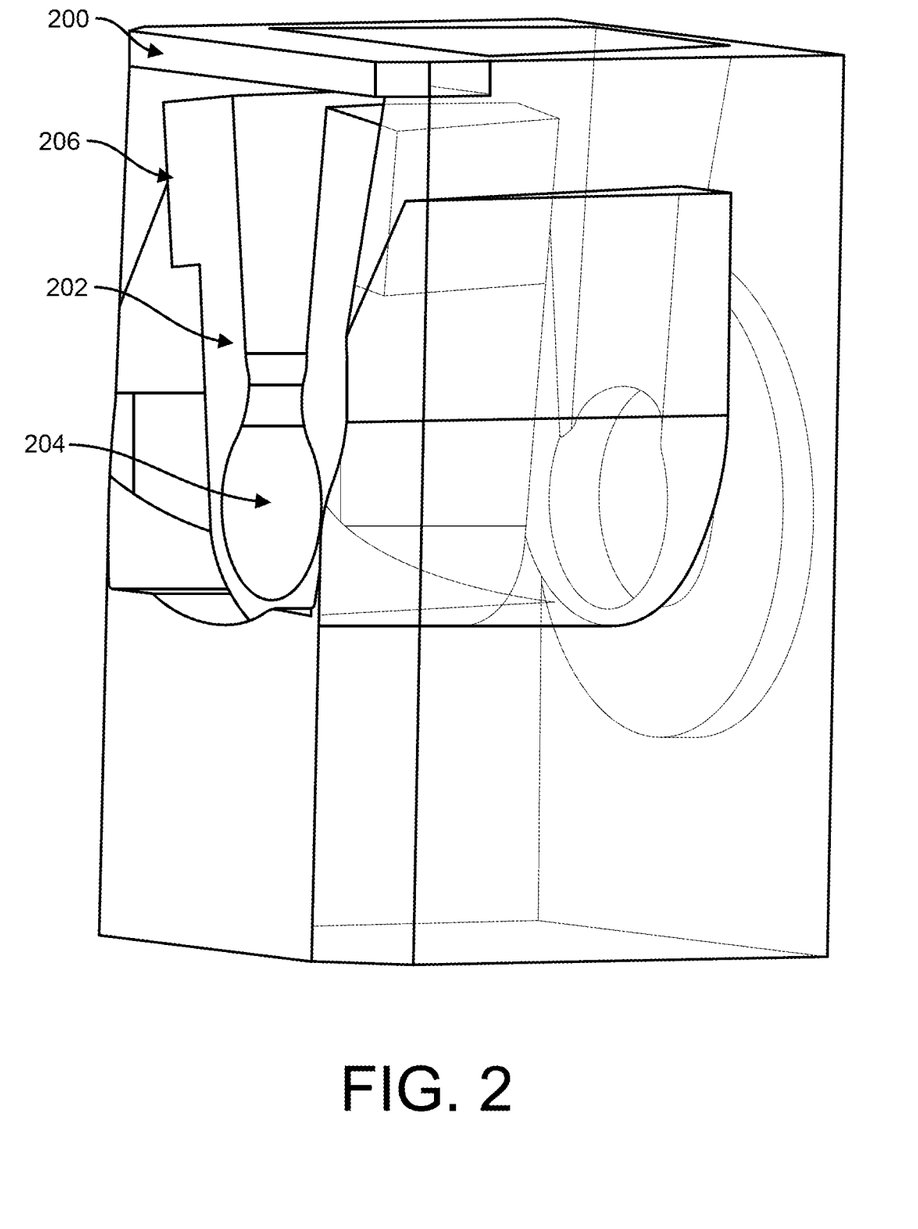
FIG. 2 is a perspective view of an illustration of an example connector port and clamp, in accordance with various aspects of the present disclosure.

FIG. 2 is a perspective view of an illustration of an example connector port 200 and clamp 202, in accordance with various aspects of the present disclosure. The connector port 200 may be arranged within a header that forms a portion of a housing of an implantable medical device as shown above with reference to FIG. 1. The connector port 200, arranged within the header, is configured to couple an implantable lead to the header (and to the implantable medical device).

As shown in FIG. 2, the clamp 202 is arranged within the connector port 200. The clamp 202 is configured to secure the implantable lead with the header in response to frictional engagement between a portion of the implantable lead and the clamp 202. In certain instances, the clamp 202 includes an engagement portion 204 configured to receive the portion of the implantable lead. As shown, the engagement portion 204 may be substantially circular in shape (although the engagement portion 204 may be of any shape that may reduce in dimension or diameter such as a polygonal shape). In addition, the portion of the lead that is engaged with the engagement portion 204 of the clamp 202 may be a terminal connector assembly (e.g., terminal pin) as described above with reference to FIG. 1. In certain instances, a circumference of the engagement portion 204 may be approximately equal to a circumference of the terminal connector assembly (e.g., terminal pin) of the lead. In other instances, the engagement portion 204 may smaller than a circumference of the terminal connector assembly (e.g., terminal pin) of the lead. In other instances, the engagement portion 204 may larger than a circumference of the terminal connector assembly (e.g., terminal pin) of the lead.

In certain instances, the clamp 202 also includes a securement portion 206. The securement portion 206 of the clamp 202 may be configured to reduce a diameter (or dimension) of the engagement portion 204 to frictionally engage the portion of the implantable lead. In certain instances, the securement portion 206 is configured to reduce the diameter of the engagement portion 204 in response to the terminal connector assembly of the lead being arranged within the engagement portion 204. The terminal connector assembly of the lead, as noted above, may be sized relative to the engagement portion 204 such that the circumference or diameter of the engagement portion 204 is slightly smaller than the terminal connector assembly of the lead. Thus, when the terminal connector assembly of the lead is arranged or forced into the engagement portion 204 of the clamp 202, forces act or attempts to expand the circumference or diameter of the engagement portion 204. The securement portion 206 is configured to maintain or reduce the circumference or diameter of the engagement portion 204 as the terminal connector assembly of the lead is arranged or forced into the engagement portion 204 of the clamp 202 and as the terminal connector assembly of the lead is withdrawn from the clamp 202. In this manner, the terminal connector assembly of the lead is secured within the clamp 202 and to the connector port 200.

Figure 3:
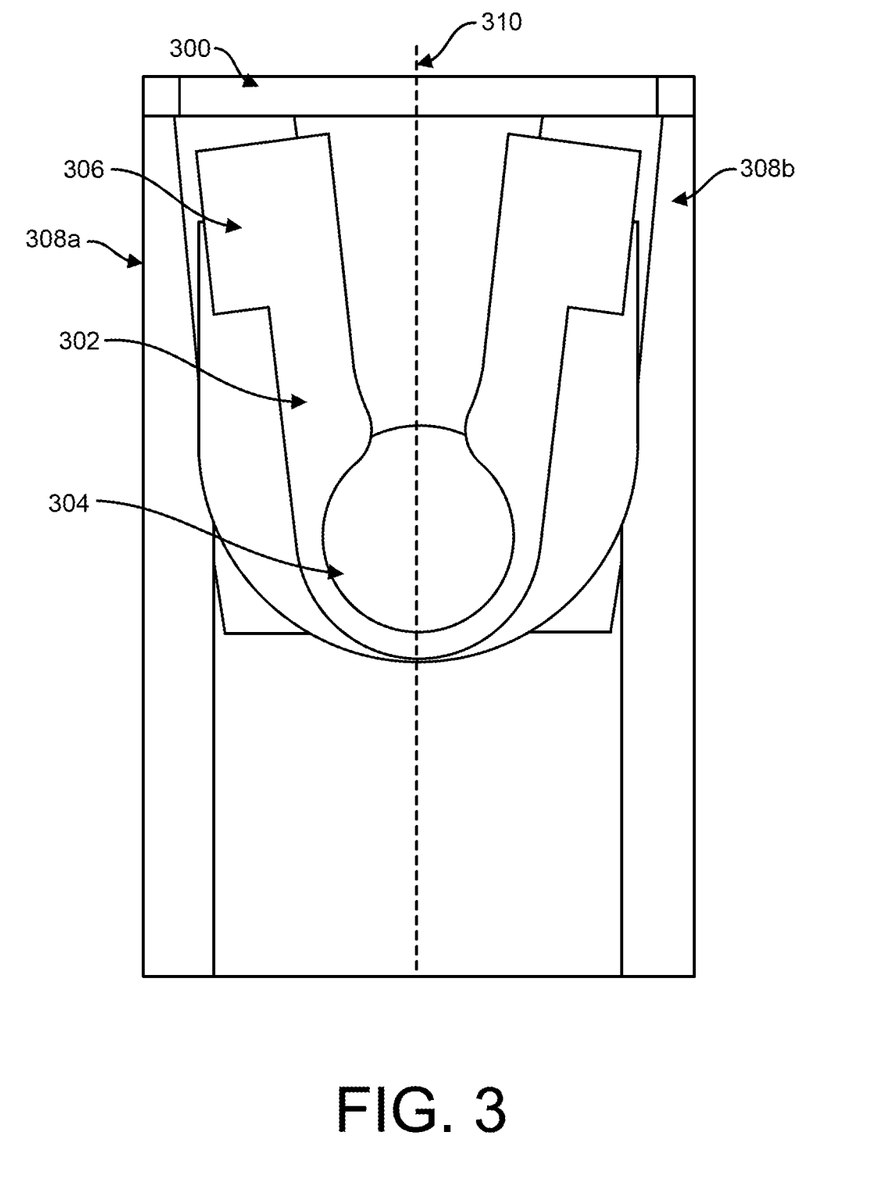
FIG. 3 is an end view of an illustration of an example connector port and clamp, in accordance with various aspects of the present disclosure.

FIG. 3 is an end view of an illustration of an example connector port 300 and clamp 302, in accordance with various aspects of the present disclosure. The connector port 300 may be arranged within a header that forms a portion of a housing of an implantable medical device as shown above with reference to FIG. 1. The connector port 300, arranged within the header, is configured to couple an implantable lead to the header (and to the implantable medical device).

In certain instances, the securement portion 306 is configured to apply force inwardly relative to the connector port 300 in response to engagement between the portion of the implantable lead and the engagement portion 304. As shown in FIG. 3, the securement portion 306 may be configured to move inwardly relative a longitudinal axis 310 of the connector port 300. In certain instances, the securement portion 306 of the clamp 302 are configured to contact interior walls 308a, 308b of the connector port 300 in response to the portion of the lead being arranged within the engagement portion 304. The securement portion 306 is forced against the interior walls 308a, 308b of the connector port 300, which reduce the diameter of the engagement portion 304 to frictionally engage the portion of the implantable lead. As noted above, when the terminal connector assembly of the lead is arranged or forced into the engagement portion 304 of the clamp 302, forces act or attempt to expand the circumference or diameter of the engagement portion 304. The securement portion 306 is forced against the interior walls 308a, 308b of the connector port 300 to maintain or reduce the diameter of the engagement portion 304 rather than allow expansion of the engagement portion 304.

In certain instances and as described in further detail below, the portion of the lead may secured within the engagement portion 304 of the clamp 302 after entry of the portion of the lead into the engagement portion 304. Forces acting on the lead in the direction opposite that of the lead being entered into the engagement portion 304 will not remove the portion of the lead from the engagement portion 304. In certain instances, a force applied in the direction opposite of entry may increase the force applied to the portion of the lead by the engagement portion 304. The force in the opposite direction of entry may increase an amount of force moving the securement portion 306 against the interior walls 308a, 308b of the connector port 300. This additional or increased force may further reduce the diameter of the engagement portion 304.

Figure 4:
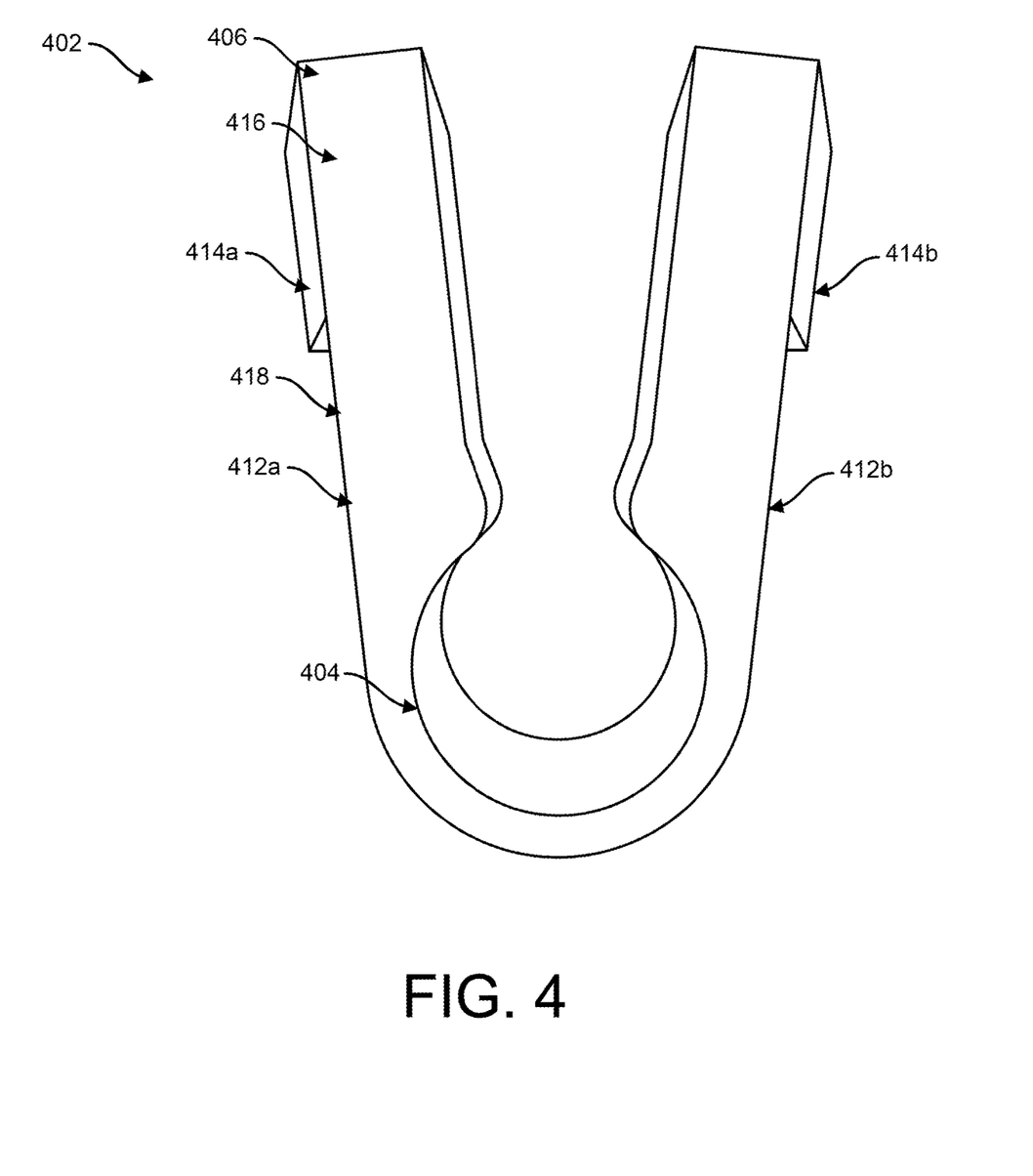
FIG. 4 is an end view of an illustration of an example clamp, in accordance with various aspects of the present disclosure.

FIG. 4 is an end view of an illustration of an example clamp 402, in accordance with various aspects of the present disclosure. The clamp 402, as discussed in detail above, includes an engagement portion 404 and a securement portion 406. The securement portion 406 is configured to apply force inwardly relative to a connector port in response to engagement between the portion of the implantable lead and the engagement portion 404.

As shown in FIG. 4, the securement portion 406 extends outwardly radially relative to the engagement portion 404. The securement portion 406 may extend at an angle relative to an exterior portion of the engagement portion 404. For example, the securement portion 406 includes angled surfaces 412a, 412b extending from the engagement portion 404. The angled surfaces 412a, 412b may be configured to apply force against interior surfaces of the connector port, as shown in FIG. 3, to reduce the diameter of the engagement portion 404 to frictionally engage the portion of the implantable lead. The interior surfaces of the connector port stop the angled surfaces 412a, 412b from moving outwardly thereby reducing the diameter of the engagement portion 404.

In certain instances, the securement portion 406 includes at least one wedge portion 414a, 414b that facilitate reducing the diameter of the engagement portion 404. In certain instances, each of the angles surfaces 412a, 412b include wedge portions 414a, 414b. In addition, the wedge portions 414a, 414b may be protrusions relative to a surface of the clamp 402. In certain instances, the clamp 402 includes a first surface 416 and a second surface 418. The wedge portions 414a, 414b may protrude outwardly from the first surface 416 or the second surface 418 relative to other sections of the angled surfaces 412a, 412b.

The wedge portions 414a, 414b (or protrusions) are configured to reduce the diameter of the engagement portion 404 to frictionally engage the portion of the implantable lead by contacting the interior surfaces of the connector port to force against the opposing faces (which may be angled) on the connector port to reduce the diameter of the engagement portion 404.

In certain instances, the clamp 402 may include surface structures (e.g., surface roughness, texture, barbs) arranged within the clamp 402 to facilitate frictional engagement between the portion of the lead and the clamp 402. The surface structures may be arranged within the engagement portion 404, for example.

FIG. 5 is a cross-sectional view of an illustration of an example connector port 500 and clamp 502, in accordance with various aspects of the present disclosure. As shown in FIG. 5, the clamp 502, arranged within the connector port 500, and configured to secure the implantable lead with the header. In response to frictional engagement between a portion of the implantable lead (e.g., terminal connector 308) and the clamp 502. An engagement portion 504 is configured to receive the terminal connector 508 and a securement portion 506a, 506b of the clamp 502 may be configured to reduce a diameter of the engagement portion 504 to frictionally engage the terminal connector 508.

The securement portion 506a, 506b may include two surfaces that are configured to contact interior surfaces 520a, 520b of the connector port 500. In certain instances, the securement portion 506a, 506b is configured to reduce the diameter of the engagement portion 204 in response to the terminal connector 508 of the lead being arranged within the engagement portion 504. In certain instances, the engagement portion 504 may be sized relative to the terminal connector 508 such that the circumference or diameter of the engagement portion 504 is slightly smaller or approximately the same size as than the terminal connector 508 of the lead. Thus, when the terminal connector 508 of the lead is arranged or forced into the engagement portion 504 of the clamp 502, forces act or attempt to expand the circumference or diameter of the engagement portion 504. The securement portion 506a, 506b is configured to maintain or reduce the circumference or diameter of the engagement portion 504 as the terminal connector assembly of the lead is arranged or forced into the engagement portion 504 of the clamp 502.

In certain instances, the securement portion 506a, 506b is forced into the interior surfaces 520a, 520b of the connector port 500 to force to reduce the diameter of the engagement portion 504. The securement portion 506a, 506b, which may be angled surfaces as described above with reference to FIG. 4, may be configured to apply force against interior surfaces of the connector port 500 to reduce the diameter of the engagement portion 404 to frictionally engage the portion of the implantable lead. The interior surfaces 520a, 520b of the connector port 500 stop the securement portion 506a, 506b from moving outwardly thereby reducing the diameter of the engagement portion 504.

In certain instances the connector port 500 includes a proximal end 530 and a distal end 532 with the clamp 502 being between the proximal end 530 and the distal end 532 of the connector port 500. The clamp 502 is configured to maintain the terminal connector 508 of the lead within the connector port 500. In certain instances, the terminal connector 508 of the lead may be locked in place in response to forces acting on the implantable lead in direction opposite the distal end. In other instances, the terminal connector 508 of the lead may be locked in place in response to initial movement of the terminal connector 508 of the lead into the clamp 502. The clamp 502 may be configured to maintain securement between the terminal connector 508 of the lead and the connector port 500 in the absence of disengagement of the clamp 502. As described in further detail below, intervention of a physician or user using a release mechanism may disengage the clamp 502 to allow release of the terminal connector 508 of the lead.

In certain instances, the securement portion 506a, 506b is configured to apply force inwardly relative to the connector port 500 in response to engagement between the terminal connector 508 of the lead and the engagement portion 504. In certain instances, the clamp 502 is configured to increase frictional hold on the terminal connector 508 of the lead in response to forces acting on the lead in direction opposite the distal end 532 of the connector port 500. In addition, the clamp 502 may be configured to progressively increase the frictional hold on the terminal connector 508 of the lead in response to increasing forces acting on the lead in direction away opposite the distal end 532.

In certain instances, the interior surfaces 520a, 520b of the connector port 500 may be angled to increase an interior diameter of the connector port 500 from the proximal end 530 to the distal end 532. Pulling back on the lead will force the clamp along the angled interior surfaces 520a, 520b may progressively increase the terminal connector 508 of the lead. The securement portion 506a, 506b of clamp 502 may be drawn toward the proximal end 530 of the connector port 500 in response to forces on the lead in to remove the lead from the clamp 502.

With the angled interior surfaces 520a, 520b decreasing the diameter of the connector port 500 toward the proximal end 530, pulling back on the lead will increase forces between the securement portion 506a, 506b and the interior surfaces 520a, 520b progressively. As noted above, the forces between the securement portion 506a, 506b and the interior surfaces 520a, 520b decrease the diameter of the engagement portion 504. The amount of forces between the securement portion 506a, 506b and the interior surfaces 520a, 520b corresponds to forces acting to decrease the diameter of the engagement portion 504. Therefore, forces acting to remove the lead from the clamp 502 may increase frictional engagement between the engagement portion 504 and the terminal connector 508 of the lead.

FIG. 6 is a side cross-sectional view of an illustration of an example header 650, connector port 600, and clamp 602, in accordance with various aspects of the present disclosure. As shown, the connector port 600 is arranged within the header 650 and configured to couple an implantable lead to the header 650. The clamp 602 is arranged within the connector port 600 configured to releasably secure the implantable lead with the header in response to frictional engagement between a portion of the implantable lead (e.g., a terminal connector 608) and the clamp 502. The frictional engagement between the terminal connector 608 may occur in response a first force applied to the implantable lead to engage the engagement portion in a first direction 652.

In certain instances, a release mechanism 640 is arranged with the header 650. The release mechanism 640 may be configured to allow release of the frictional engagement between the clamp 602 and the terminal connector 608 to allow removal of the implantable lead from the clamp 602 in response a second force applied to the implantable lead in a second direction 654 opposite the first direction 652.

The release mechanism 640 may be configured to disengage the clamp 602 in response to a user interaction to a force applied to the release mechanism. In certain instances, the release mechanism 640 includes a button configured to disengage the clamp 602 in response to the force applied by the user. In addition, the release mechanism 640 may include at least one release portion 642 configured interact with the clamp 602 to block frictional engagement between the terminal connector 608 of the lead and the clamp 602.

In certain instances, the clamp 602 is configured to allow engagement between the terminal connector 608 of the lead and the clamp 602 while the force is applied to the release mechanism 640. In addition, the clamp 602 may lock the terminal connector 608 of the lead within the clamp 602 in response to release of the force on the release mechanism 640. In these instances, an engagement portion 604 of the clamp 602 may expand in response to the force on the release mechanism 640. The clamp 602 and the engagement portion 604 may be biased toward a locking position, in these instances, and the release mechanism 640 may open and close the clamp 602 and the engagement portion 604 as described in further detail below with reference to FIG. 7

As noted above, the terminal connector 608 of the lead may be locked in place in response to initial movement of the terminal connector 608 of the lead into the clamp 602 in the first direction 652. In addition and as discussed above, the terminal connector 608 of the lead may be locked in place in response to initial movement of the terminal connector 608 of the lead into the clamp 602 in the first direction 652, and a second force applied in the second direction 654. This action reduces the diameter of engagement portion 604 to frictionally engage the terminal connector 608. In either instance, the release portion 642 may be configured interact with the clamp 602 to enable disengagement of the terminal connector 608 in response to the user pressing the button. The release portion 642, in certain instances, may block forces between the securement portion 506 of the clamp and interior surfaces of the connector port 600 that would decrease the diameter of the engagement portion 604. This action may allow release of the terminal connector 608 from the clamp 602.

As noted above, the interior surfaces of the connector port 600 may taper inwardly toward a proximal end (e.g., in the second direction 654). In these instances, the release portion 642 may block the clamp 602 (e.g., the securement portion 606) from being drawn in the second direction 654. In this manner, the forces acting to reduce the securement portion 606, which, in turn reduce a diameter of the engagement portion 604, are blocked.

Figure 7:
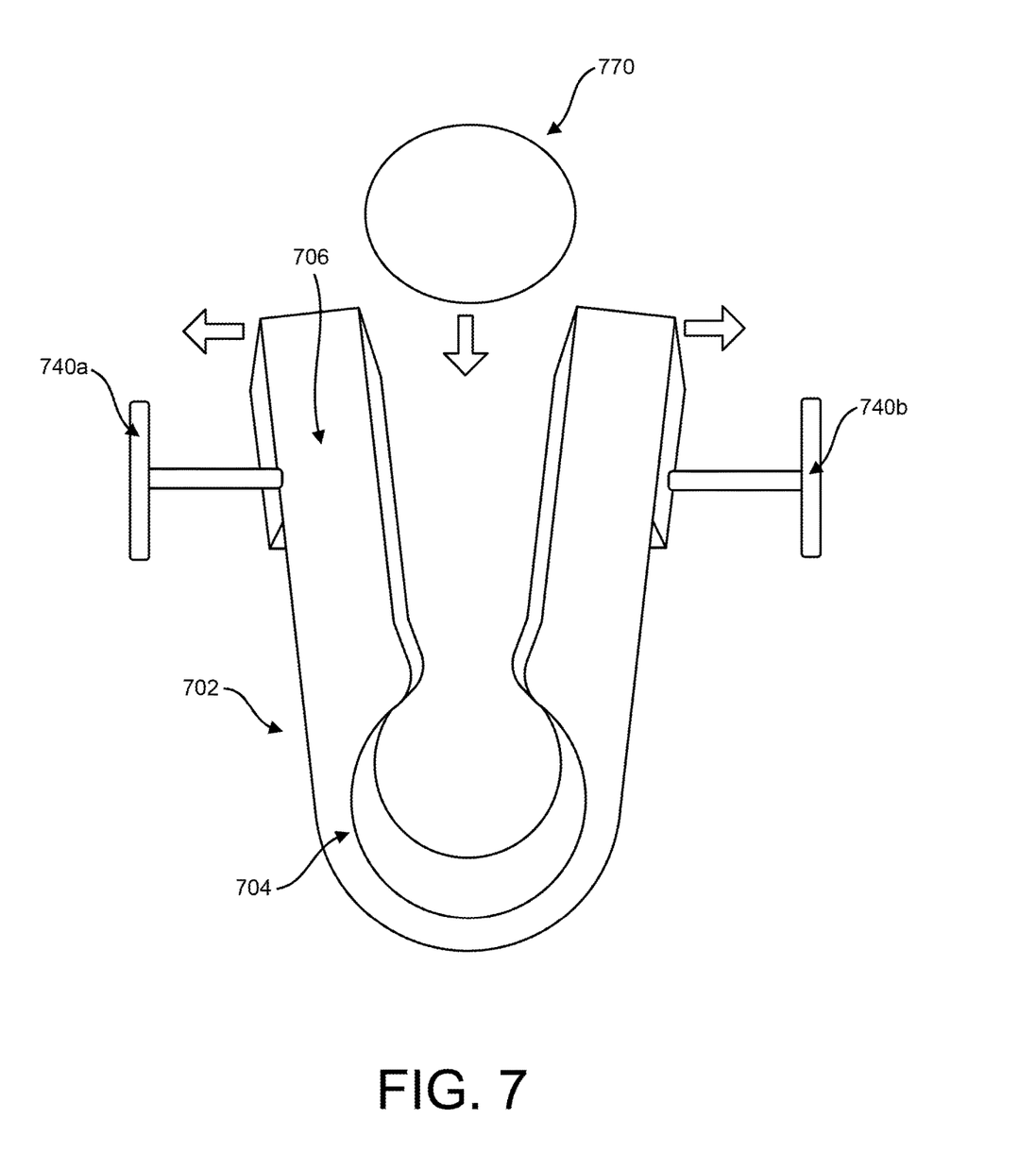
FIG. 7 is an illustration of an example release mechanism and clamp, in accordance with various aspects of the present disclosure.

FIG. 7 is an illustration of an example release mechanism 770 and clamp 702, in accordance with various aspects of the present disclosure. The clamp 702, as discussed in detail above, includes an engagement portion 704 and a securement portion 706. The securement portion 706 is configured to apply force inwardly relative to a connector port in response to engagement between the portion of the implantable lead and the engagement portion 704. As noted above, a terminal connector of a lead may be locked in place in response to initial movement of the terminal connector of the lead into the clamp 702 in a first direction. Springs 740a, 740b may be arranged within the connector port to bias the clamp 702 into a locked position. The springs 740a, 740b, more specifically, may be configured to bias the securement portion 706 to reduce the diameter of the engagement portion 704 to facilitate frictional engagement between the portion of the lead and the engagement portion 704.

In certain instances, the springs 740a, 740b may not bias the securement portion 706 to the reduced diameter, and pressing the release mechanism 770 may force the springs 740a, 740b (or other structures that hold a force applied thereto) inwardly to reduce the diameter of the engagement portion 704 to facilitate frictional engagement between the portion of the lead and the engagement portion 704 (e.g., the terminal connector of the lead is forced into the clamp 702 and pressing of the release mechanism 770 closes the clamp 702 about the terminal connector of the lead and locks the terminal connector in place). Pressing the release mechanism 770 a second time may release the terminal connector of the lead from the clamp 702.

In certain instances, the clamp 702 is configured to allow engagement between the portion of the implantable lead and the clamp while the force is applied to the release mechanism 770, and lock the portion of the implantable lead within the clamp 702 in response to release of the force on the release mechanism 770. In certain instances, the release mechanism 770 (e.g., button or buttons arranged on the header) may move inwardly into the securement portion 706 to allow the engagement portion 704 of the clamp 702 to expand in diameter (e.g., unbiasing the springs 740a, 740b). In certain instances, a force is to be applied to the release mechanism 770 to allow the portion of the lead to enter the clamp 702. In other instances, the portion of the lead may enter the clamp 702 in the absence of force applied to the release mechanism 770. In either instances, the force applied to the release mechanism 770 allows the portion of the lead to be released by allowing expansion and disengagement of the engagement portion 704.

Figure 8:
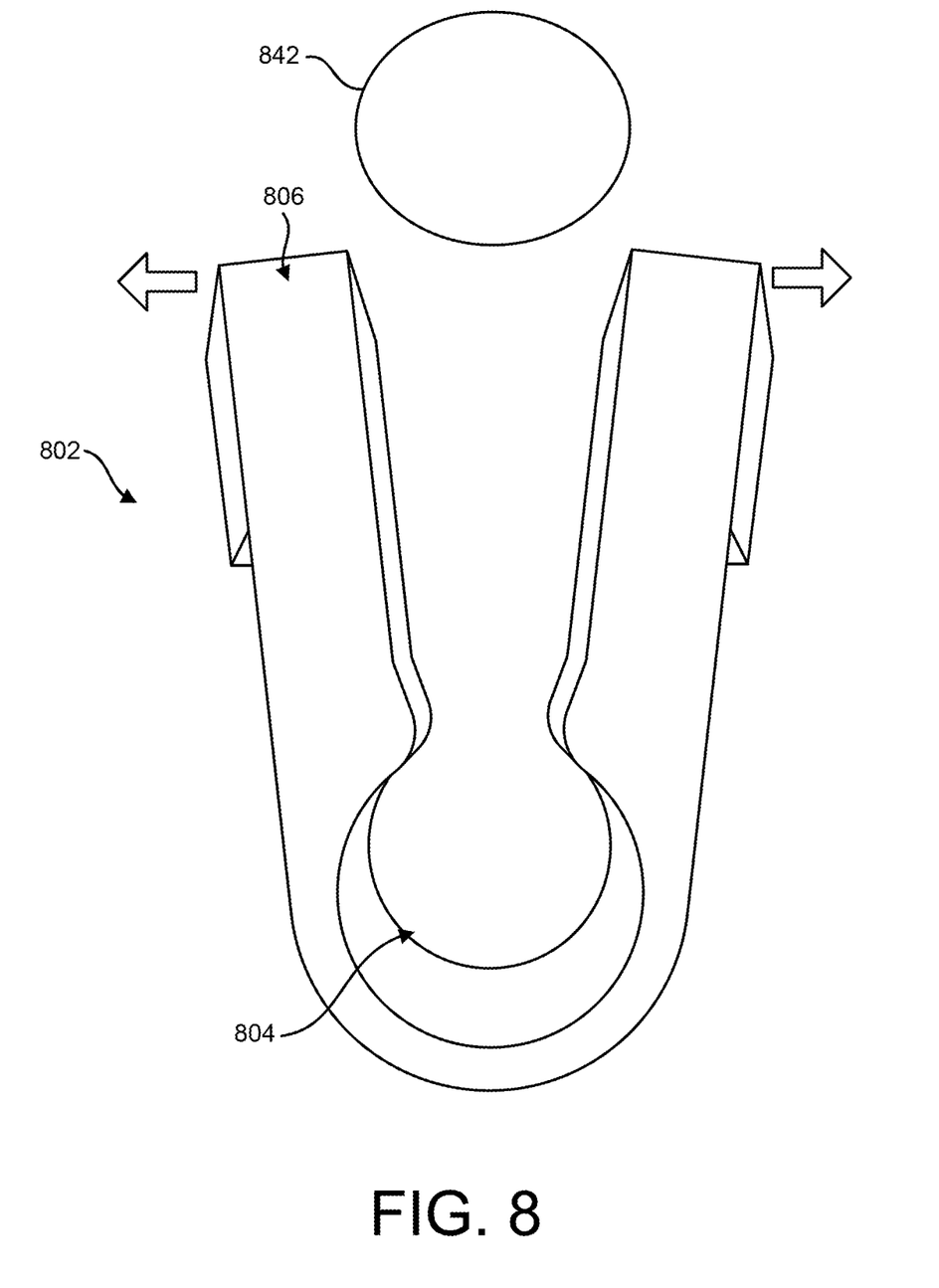
FIG. 8 is an illustration of another example release mechanism and clamp, in accordance with various aspects of the present disclosure.

FIG. 8 is an illustration of another example release mechanism 842 and clamp 802, in accordance with various aspects of the present disclosure. The clamp 802, as discussed in detail above, includes an engagement portion 804 and a securement portion 806.

The securement portion 806 is configured to apply force inwardly relative to a connector port in response to engagement between the portion of the implantable lead and the engagement portion 804. As noted above, a terminal connector of a lead may be locked in place in response to initial movement of the terminal connector of the lead into the clamp 802 in a first direction.

In certain instances, the clamp 802 is configured to allow engagement between the portion of the implantable lead and the clamp while the force is applied to the release mechanism 842, and lock the portion of the implantable lead within the clamp 802 in response to release of the force on the release mechanism 842. In certain instances, a force is to be applied to the release mechanism 842 to allow the portion of the lead to enter the clamp 802. In other instances, the portion of the lead may enter the clamp 802 in the absence of force applied to the release mechanism 842. In either instances, the force applied to the release mechanism 842 allows the portion of the lead to be released by allowing expansion and disengagement of the engagement portion 804. The release mechanism 842 may be associated with a button or other structure on the header that the user can interact with to open the securement portion 806 of the clamp 802.

The release mechanism 842 is configured interact with the securement portion 806 to enable disengagement of the portion of the implantable lead from the engagement portion 804. The release mechanism 842 may be configured to block movement of the securement portion 806 to expand the engagement portion 804 and enable disengagement of the portion of the implantable lead from the engagement portion 804. The release mechanism 842 may spread outward the securement portion 806 to allow movement (and release) of the portion of the lead.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device comprising:
a housing; and
a header arranged with the housing;
a connector port arranged within the header and configured to couple an implantable lead to the header;
a clamp arranged within the connector port configured to secure the implantable lead with the header, the clamp including an engagement portion configured to receive a portion of the implantable lead and a securement portion configured to reduce a diameter of the engagement portion to frictionally engage the portion of the implantable lead; and a release mechanism arranged on the header and configured to disengage the clamp in response to a force applied to the release mechanism to release the portion of the implantable lead from the clamp.

2. The implantable medical device of claim 1, wherein the securement portion is configured to apply force inwardly relative to the connector port in response to the engagement between the portion of the implantable lead and the engagement portion.

3. The implantable medical device of claim 2, wherein the securement portion includes angled surfaces extending from the engagement portion, and the angled surfaces are configured to apply force against opposing angled faces on the connector port to reduce the diameter of the engagement portion to frictionally engage the portion of the implantable lead.

4. The implantable medical device of claim 3, wherein the angled surfaces of the securement portion are configured to apply force inwardly relative to the connector port to reduce the diameter of the engagement portion.

5. The implantable medical device of claim 3, wherein the angled surfaces of the securement portion each include a protrusion extending outwardly relative to the angled surfaces of the securement portion configured to apply force against the opposing angled faces on the connector port to reduce the diameter of the engagement portion.

6. The implantable medical device of claim 1, wherein the release mechanism includes a button configured to disengage the clamp in response to the force applied by a user.

7. The implantable medical device of claim 1, wherein the release mechanism includes at least one release portion configured to interact with the securement portion to enable disengagement of the portion of the implantable lead from the engagement portion.

8. The implantable medical device of claim 7, wherein the at least one release portion is configured to block movement of the securement portion to expand the engagement portion and enable disengagement of the portion of the implantable lead from the engagement portion.

9. The implantable medical device of claim 1, wherein the clamp is configured to allow engagement between the portion of the implantable lead and the engagement portion while the force is applied to the release mechanism, and lock the portion of the implantable lead within the engagement portion in response to the release of the force on the release mechanism.

10. The implantable medical device of claim 1, further comprising a spring arranged within the connector port and configured to bias the securement portion to reduce the diameter of the engagement portion to facilitate frictional engagement between the portion of the implantable lead and the engagement portion.

11. The implantable medical device of claim 10, wherein the securement portion is configured to lock the portion of the implantable lead within the engagement portion in response to the engagement between the portion of the implantable lead and the securement portion.

12. The implantable medical device of claim 1, wherein the securement portion is configured to lock the portion of the implantable lead within the engagement portion in response to a first force applied to the implantable lead in a first direction to engage the engagement portion and a second force applied to the implantable lead in a second direction opposite the first direction.

13. An implantable medical device comprising:
a housing; and
a header arranged with the housing;
a connector port arranged within the header and configured to couple an implantable lead to the header;
a clamp arranged within the connector port configured to releasably secure the implantable lead with the header in response to frictional engagement between a portion of the implantable lead and the clamp in response to a first force applied to the implantable lead in a first direction; and
a release mechanism configured to allow release of the frictional engagement between the clamp and the portion of the implantable lead and allow removal of the implantable lead from the clamp in response to a second force applied to the implantable lead in a second direction opposite the first direction.

14. The implantable medical device of claim 13, wherein the release mechanism is configured to disengage the clamp in response to a force applied to the release mechanism to release the portion of the implantable lead from the clamp.

15. The implantable medical device of claim 14, wherein the release mechanism includes a button configured to disengage the clamp in response to the force applied by a user.

16. The implantable medical device of claim 15, wherein the release mechanism includes at least one release portion configured to interact with the securement portion to enable disengagement of the portion of the implantable lead from the clamp in response to the user pressing the button.

17. A method of coupling an implantable lead to an implantable medical device, the method comprising:
coupling the implantable lead to the implantable medical device by moving the implantable lead in a first direction into a connector port arranged within a header of the implantable medical device; and
engaging a portion of the implantable lead with a clamp arranged within the connector port in response to frictional engagement between the portion of the implantable lead and the clamp.

18. The method of claim 17, further comprising releasing the portion of the implantable lead by applying a force to a release mechanism arranged with the header.

19. The method of claim 18, wherein applying the force to the release mechanism includes pressing a button to block the frictional engagement between the clamp and the portion of the implantable lead.

* * * * *